United States Patent [19]
Keefe

[11] Patent Number: 5,651,371
[45] Date of Patent: Jul. 29, 1997

[54] SYSTEM AND METHOD FOR MEASURING ACOUSTIC REFLECTANCE

[75] Inventor: Douglas H. Keefe, Seattle, Wash.

[73] Assignee: The University of Washington, Seattle, Wash.

[21] Appl. No.: 453,075

[22] Filed: May 26, 1995

Related U.S. Application Data

[62] Division of Ser. No. 254,311, Jun. 6, 1994, abandoned.

[51] Int. Cl.⁶ .................................................. A61B 5/12
[52] U.S. Cl. ................................. 128/746; 73/585
[58] Field of Search ........................ 128/746; 73/585, 73/587, 589, 645–648

[56] References Cited

U.S. PATENT DOCUMENTS

| | | | |
|---|---|---|---|
| 4,289,143 | 9/1981 | Canavesio et al. | 128/746 |
| 4,374,526 | 2/1983 | Kemp | 128/746 |
| 4,459,996 | 7/1984 | Teele | 128/746 |
| 4,601,295 | 7/1986 | Teele | 128/746 |
| 4,809,708 | 3/1989 | Geisler et al. | 128/746 |
| 4,884,447 | 12/1989 | Kemp et al. | 73/585 |
| 5,105,822 | 4/1992 | Stevens et al. | 128/746 |

OTHER PUBLICATIONS

Rabinowitz, William M., "Measurement of the acoustic input immittance of the human ear*ᵃ*", *J. Acoustical Society of America* 70(4):1025–1035, 1981.

Biarge, Victoria Rodellar and Pedro Gomez Vilda., "Experimental system for registering and processing the stimulated emissions from within the Auditory System in the characterization of its Transmission Pattern.," *IEEE* 1:25–28, 1985.

Stevens, Kenneth N. et al., "Calibration of ear canals for audiometry at high frequencies", *J. Acoustical Society of America*, 81: 470–84, 1987.

Whitehead, M.L., B. B. Stagner, Brenda L. Lonsbury–Martin, and Glen K. Martin, "Measurement of Otoacoustic Emissions For Hearing Assessment," *IEEE Engineering In Medicine and Biology* 13:210–226, 1994.

P. Bray, "Click evoked otoacoustic emissions and the development of a clinical otoacoustic hearing test instrument," doctoral dissertation, University of London, London, England, 1989.

I. Blood et al., "Acoustic Otoscopic Measures in Toddler Population," Poster presented at the American Speech Language Hearing Association, Seattle, Washington, Nov., 1990.

(List continued on next page.)

*Primary Examiner*—Max Hindenburg
*Attorney, Agent, or Firm*—Seed and Berry LLP

[57] ABSTRACT

A system and method of measuring the linear and nonlinear response of an unknown acoustic termination uses a small probe assembly containing a sound source and microphone to determine the reflection function of the unknown acoustic termination. The probe assembly is used with a calibration tube to calculate an electrical signal that will provide a desired acoustic stimulus signal to the acoustic termination. The calibration tube is also used to characterize the signal processing properties of the sound source and microphone, as well as other associated signal processing circuits such as amplifiers, filters, and the like. The calibrated system is subsequently coupled to the unknown acoustic termination to deliver the acoustic stimulus signal. The reflection function is indicative of the power transferred to the unknown acoustic termination. The measurement of the linear transfer characteristic is applicable to any unknown acoustic termination such as a musical instrument or the auditory system. The probe assembly is sized to be positioned directly within the outer portion of the ear and measure the linear characteristics of the ear. The system is further able to measure the nonlinear transfer characteristics of the ear by measuring the linear response at multiple levels of the acoustic stimulus. The system is particularly useful in testing the response of the middle ear and inner ear of humans or other animals.

30 Claims, 6 Drawing Sheets

OTHER PUBLICATIONS

D. Keefe et al., "Method to measure acoustic impedance and reflection coefficient," *J. Acoust. Soc. Am* 91(1):470–485, 1992.

D. Jurzitza and W. Hemmert, "Quantitative Measurements of Simultaneous Evoked Otoacoustic Emissions," *Acustica*, 77:93–99, 1992.

M. Joswig, "Impulse Response Measurement of Individual Ear Canals and Impedances at the Eardrum in Man," *Acustica*, 77:270–282, 1993.

C. Shera and G. Zweig, "Noninvasive measurement of the cochlear traveling-wave ratio," *J. Acoust. Soc. Am.* 93(6):3333–3352, 1993.

D. Keefe et al., "Ear-canal impedance and reflection coefficient in human infants and adults," *J. Acoust. Soc. Am* 94(5):2617–2638, 1993.

P. Dallos. "On the Generation of Odd–Fractional Subharmonics," *J. Acoust. Soc. Am.*, 40:1381–1391, 1966.

P. Dallos. *The Auditory Periphery*, Academic Press, U.S.A., 1973, pp. 448–464.

J.P. Wilson and J.R. Johnstone, "Basilar membrane and middle-ear vibration in guinea pig measured by capacitive probe," *J. Acoust. Soc. Am.*, 57:705–723, 1975.

D. T. Kemp and R. A. Chum. "Observations on the generator mechanism of stimulus frequency acoustic emissions—two tone suppression." In E. deBoer and M. A. Viergever (eds.), *Psycho–physical, Physiological and Behavioral Studies in Hearing*, Delft Univ. Press, pp. 34–41, 1980.

P. Dallos. Comment on "Observations on the generator mechanism of stimulus frequency acoustic emissions—two tone suppression" (D.T. Kemp and R. Chum). In E. deBoer and M. A. Viergever, (eds.), *Psychophysical, Physiological and Behavioral Studies in Hearing*, Delft Univ. Press, p. 42, 1980.

P.M. Zurek. "Acoustic emissions from the ear: A summary of results from humans and animals," *J. Acoust. Soc. Am.*, 78:340–344, 1985.

SYSTEM AND METHOD FOR MEASURING ACOUSTIC REFLECTANCE

CROSS-REFERENCE TO RELATED APPLICATION

This application is a division of U.S. patent application Ser. No. 08/254,311, filed Jun. 6, 1994 now abandoned.

TECHNICAL FIELD

The system relates generally to a system and method for measuring acoustic reflectance, and more particularly, to a system and method for measuring the linear and nonlinear acoustic reflectance of the ear.

BACKGROUND OF THE INVENTION

Many hearing disorders are based upon abnormal states of the external, middle or inner ear. Quantitative data can be obtained by utilizing acoustic signals and responses measured in the ear canal. This data can be combined with other measurements to provide information used in the detection and diagnosis of hearing disorders, and the clinical management of existing hearing disorders.

One of the most basic acoustic tests has to do with the characterization of the linear response of the ear, assessed by measurements of the impedance, reflectance, reflectometry, impulse response and/or reflection function. The standard clinical impedance test is based upon tympanometry, which measures the acoustic impedance at a single frequency, or at a discrete range of frequencies. Tympanometry was developed for use in adults, and it is widely held that it is grossly inaccurate in testing neonates. One of the contributing factors is that tympanometry is dependent upon static pressurization of the ear canal, and this static pressure produces artifacts that are particularly troublesome in infants. Nonetheless, the clinical importance of measuring the linear response of the ear is well documented.

It is well known that the human ear reflects sound pressure at very long latencies, 5–20 ms, after the presentation of an acoustic stimulus in the ear canal. However, it is unknown to what extent these so-called evoked otoacoustic emissions (EOAE) represent a delayed reflection of the acoustic energy in the original stimulus (i.e., a passive model) or represent energy output from sites of power generation within the inner ear (i.e., an active-source model).

At present there is no convenient technique available to measure the linear and nonlinear responses of the ear and to diagnose clinical abnormalities in the ear. Therefore, it can be appreciated that there is a significant need for an instrument to characterize the linear and nonlinear responses of the ear. This and other advantages of the present invention will be apparent from the following detailed description taken in conjunction with the Figures.

SUMMARY OF THE INVENTION

The present invention is embodied in a system for the measurement of a linear response of an acoustic waveguide having unknown acoustical transfer characteristics comprising a probe assembly positionable in proximity with the acoustic waveguide, an acoustic source within the probe assembly to produce an acoustic stimulus and delivery the acoustic stimulus to the acoustic waveguide in response to an electrical input signal, and an acoustical energy detector within the probe assembly to detect acoustic energy signals and to convert the detected acoustical energy signals to detected electrical signals. A stimulus generator coupled to the acoustic source generates the electrical input signal. The system includes an acoustic calibration waveguide having known acoustic transfer characteristics with the acoustic calibration waveguide having a predetermined dimensions and first and second ends, with the first end being opened and the second end being closed. At a first time, the stimulus generator generates an electrical input signal when the probe assembly is positioned in the first end of the acoustic calibration waveguide. The electrical input signal has a duration selected so that the acoustic stimulus is a short duration sound field having a duration less than a propagation time required for the acoustic stimulus to travel from the acoustic source to the closed end of the acoustic calibration waveguide, be reflected form the closed end, and travel back to the acoustic energy detector. A signal processor receives and processes the detected electrical signals. At the first time, the signal processor receives and processes the detected electrical signals to determine a transfer characteristic of the acoustic source and the acoustic energy detector. The stimulus generator, at a second time, generates the electrical input signal when the probe assembly is positioned in proximity with the unknown acoustic waveguide to provide a substantially leak-proof seal. At the second time, the signal processor receives and processes the detected electrical signals to determine a transfer characteristic of the unknown acoustic waveguide.

In one embodiment, the acoustic calibration waveguide is a cylindrical tube whose open end is substantially sealed by the probe assembly. The system may also advantageously include storage means for storing the electrical input signal for use at the first and second times. The system may also store data corresponding to the transfer characteristic of the acoustic source and acoustic energy detector for use at the second time to determine the transfer characteristic of the unknown acoustic waveguide. The transfer characteristic of the unknown acoustic waveguide may include the determination of a reflection function.

In an alternative embodiment, the system uses the acoustic calibration waveguide with the known acoustic transfer characteristics to generate an acoustic stimulus signal having a predetermined pressure response. In this embodiment, the probe assembly, containing the acoustic source and the acoustic energy detector, is positioned within the acoustic calibration waveguide at the open end to provide a substantially leak-proof seal. The stimulus generator generates an electrical test signal having a selected duration so that the acoustic energy detector has an initial response due only to acoustic energy from the acoustic source and not from acoustic energy reflected from the closed end of the acoustic calibration waveguide. The acoustic energy detector has a subsequent response due only to acoustic energy reflected from the closed end of the acoustic calibration waveguide and not from acoustic energy from the acoustic source. The initial response in the subsequent response form a total pressure response to the electrical test signal. The signal processor receives the detected electrical signals corresponding to the total response, the electrical test signal itself, and a desired total response. The signal processor determines an electrical stimulus signal that will produce the desired total pressure response when the electrical stimulus signal is applied to the acoustic source.

In a preferred embodiment, the acoustic calibration waveguide is at least 25 cm in length. In one embodiment, the acoustic calibration waveguide is a cylindrical calibration tube. The unknown acoustic waveguide may be a human ear comprising an ear canal, a middle ear and an inner ear. In this embodiment, the system determines the linear transfer characteristics of the middle ear. In an alternative embodiment, the unknown acoustic waveguide is a musical instrument air column.

In yet another embodiment, the desired total response signal is a band-limited impulse signal. In this embodiment, the signal processor determines the electrical stimulus signal using finite impulse response (FIR) signal. In an alternative embodiment, the signal processor determines the electrical stimulus signal using an infinite impulse response (IIR) signal. In yet another embodiment, the electrical test signal and the desired total response signal are both equal to the desired impulse response of an idealized filter. Embodiments of the model might include a FIR or IIR lowpass filter. Using the desired impulse response as the electrical test signal, the acoustic response is measured. In this embodiment, the signal processor calculates the electrical stimulus signal that will produce an approximation of the desired impulse response by deconvolution of the desired impulse response and the aforementioned acoustic response.

In yet another alternative embodiment, the system is positioned in the ear canal of the auditory system and measures the linear transfer characteristic of the system at a first stimulus level. The system subsequently measures the linear transfer characteristic at a second stimulus level different form the first stimulus level. The system further processes the first and second linear transfer characteristics to determine a nonlinear response of the inner ear.

DETAILED DESCRIPTION OF THE INVENTION

Figure 1:
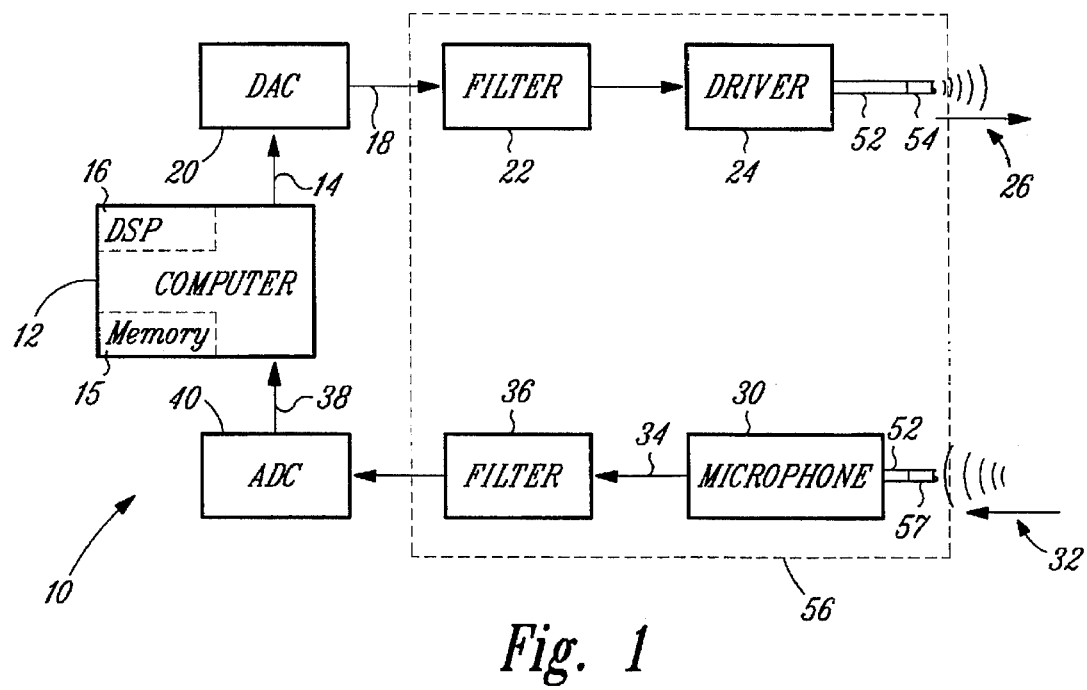
FIG. 1 is a functional block diagram of the system of the present invention.

The present system provides a novel technique for measuring the linear response of the ear in a manner is not dependent on applying static pressure to the ear canal, that provides data over most of the frequencies in the range of hearing, that is simple to use in infants or adults, and that is a rapid test. This system also provides a means to design acoustic stimuli for use in electrophysiological tests, for example, auditory brain-evoked potential response (ABR) measurement that can improve the existing types of ABR measurements. Finally, this system provides a means to extract meaningful estimates of power transfer when used in conjunction with otoacoustic emission measurements (OAE) known in the art. OAE measurements are valuable because they provide information on the state of the inner ear. An abnormal OAE measurement may be due to the state of the inner ear or middle ear, but the OAE technique cannot differentiate between these two possible sites of pathology.

The present invention provides a means of detecting abnormalities in the middle and external ear. When used in conjunction with OAE, ABR or distortion product (DP) measurements, all techniques that are said to measure abnormalities in the inner ear or auditory neural pathway, the present invention provides a more refined clinical diagnosis concerning the site of the abnormality.

As previously discussed, the measurement systems of the prior art measure OAE or EOAE based upon pressure measurements in the ear canal. These prior art measurements do not provide information about power transmitted into the middle ear and inner ear, nor do they provide information about power received from the ear in the form of emissions. Power-based techniques of the present invention give a more fundamental description of the evoked response of the ear to sound stimuli. The present invention provides practical devices to measure the power transmitted by an acoustic stimulus into the ear-canal and the power received due to the presence of EOAEs. The present invention provides a substantial improvement of the EOAE measurement technique using the more fundamental domain of power measurements rather than pressure measurements of the prior art. The system of the present invention can measure the linear and nonlinear acoustic reflectance of the ear, the combination of which is termed otoreflectance. This otoreflectance may be calculated in the frequency domain as the reflection coefficient and in the time domain as the reflection function, and other acoustic response functions such as impedance and impulse response are calculated from the reflectance using well known transformations. It allows dual measurements of the presence of a conductive impairment and the presence of a cochlear impairment, thereby giving more complete information on the state of the ear. There may be significant clinical applications in hearing for this device, not only for neonates for which the priority for early detection is so high, but also for adults including the elderly population with their specific types of hearing disorders.

The present invention is embodied in a system 10 shown in the functional block diagram of FIG. 1. A computer 12 generates a stimulus signal 14 used by the system 10. The computer 12 is a conventional device that may include memory 15 and a digital signal processor (DSP) 16 to generate the stimulus signal. The design of the stimulus signal 14 will be described in detail below. The stimulus signal 14 is convened to an analog signal 18 by a digital to analog converter (DAC) 20. The analog signal 18 can be filtered by a conventional lowpass filter 22 in a manner well known to those of ordinary skill in the art of signal processing. The output of the lowpass filter 22 is coupled to a driver 24 that transduces the electrical signal to an acoustic signal 26. It is the acoustic signal 26 that will be used to determine the linear and nonlinear responses of the ear.

The system 10 also includes a microphone 30 or other acoustic energy detector to detect a reflected acoustic signal 32 and transduces the reflected acoustic signal into a detected electrical signal 34. The acoustic energy detector may be a pressure transducer, piezoelectric transducer, or any other well-known device for transducing acoustic energy into electrical energy. The present invention is not limited by the specific form of the acoustic energy detector. The detected electrical signal 34 is filtered by a conventional lowpass filter 36 to eliminate aliasing effects and converted to a digital signal 38 by an analog to digital converter 40. The distal signal 38 is analyzed by software in the computer 12 and the DSP 16 to determine a pressure response to the stimulus signal. The system 10 determines the linear and nonlinear responses of the ear based on the pressure response of the microphone 30. Details of the signal analysis are provided below.

Figure 2:
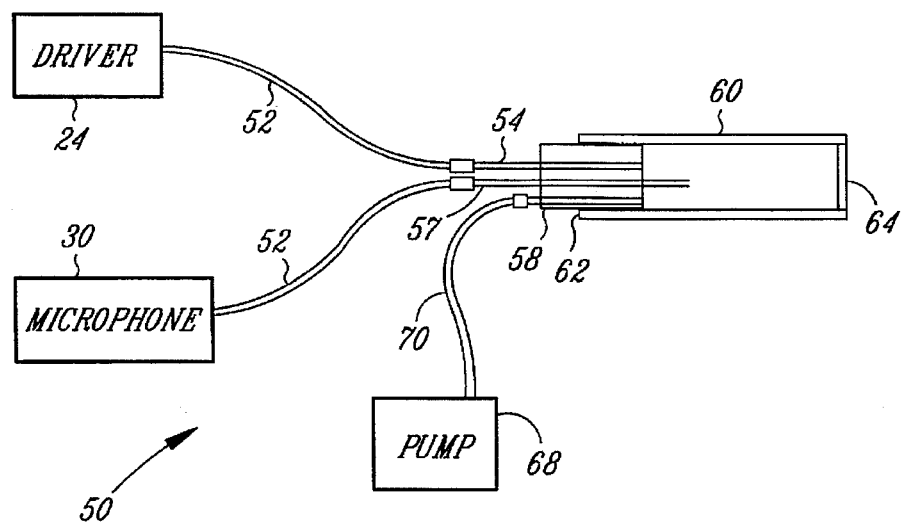
FIG. 2 is a side view of the probe assembly of the system of FIG. 1.

The driver 24 and microphone 30 are both included in a probe assembly 50, shown in FIG. 2. The driver 24 in the presently preferred embodiment of the system is an Otodynamics dual-source infant probe driver. The microphone 30 in the presently preferred embodiment of the system is a microphone included in the Otodynamics dual-source intent probe. The driver 24 and the microphone 30 are each coupled to the probe assembly 50 by small flexible tubes 52. The flexible tubes 52 are relatively short to minimize signal loss and thus maximize the signal-to-noise ratio (SNR) of the system 10. However, the precise tenth of the flexible tubes 52 is not critical because the system 10 will determine the acoustic transfer characteristics of the driver 24, microphone 30, filters 22 and 36, and the flexible tubes 52. The flexible tubes 52 couple the driver 24 and the microphone 30 to a driver probe 54 and a microphone probe 56, respectively, within the probe assembly 50. The probe assembly 50 includes a variety of standard eartips 58 fitted to accommodate the range of human ear-canal sizes from neonate to adult.

The operation of the system 10 is divided into three phases, a stimulus generation phase, a calibration phase, and an evaluation phase. In the stimulus generation phase, the system 10 uses a novel technique for generating a stimulus signal having the desired acoustical properties. Under normal use, the system 10 need only be derive the stimulus signal once at the time of assembly. The present invention also provides a novel technique for calibrating the system 10 during the calibration phase of operation. Generally, the user calibrates the system 10 for each patient. However, the system 10 provides a simple calibration procedure that easily permits such calibration. In the measurement phase of operation, the system 10 collects and analyzes data from the ear and determines therefrom information relating to the condition of the middle and inner ear. One aspect of the system 10 is its ability to measure the linear response of the ear in a manner that permits its use with existing nonlinear measures such as EOAE, DP and ABR techniques.

Measurement of Linear Reflection Function

The system 10 determines the linear response of the ear based upon the finding that the human external, middle and inner ear can be viewed as a one-dimensional acoustic waveguide. The linear acoustic response of the ear can be measured by placing the probe assembly 50 in the ear canal and conducting measurements using the system 10. The driver 24 produces a short-duration sound field (i.e., the acoustic signal 26). The microphone 30 measures the sound pressure and the system 10 derives a reflection function of the ear from the microphone response. The reflection function is used to measure the acoustic properties of the ear. In addition to the acoustic wave that propagates down the acoustic waveguide, the driver has a non-propagating mode. This non-propagating mode, sometimes called an evanescent mode, refers to acoustic signals that are non-propagating at sufficiently low frequencies such that the acoustic wavelength is small relative to the circumference of the flexible tubes 52 or ear canal. These evanescent modes describe the localized acoustic field near the probe assembly 50. Any localized, non-propagating acoustic field caused by evanescent modes in the vicinity of the probe assembly 50 can be attenuated by restricting the frequency content of the external stimulus or by other well-known methods such as drawing the microphone probe 56 slightly beyond the plane of the driver probe 54, as shown in FIG. 2. While the examples presented herein are directed to measurements of the auditory system, the principles of the present invention are applicable to any waveguide such as a musical instrument air column.

Stimulus Design Phase

As those skilled in the art can appreciate, there is some degree of variation in the acoustic and electrical response of the driver 24 and the microphone 30. For example, the frequency response of the driver 24 varies from one driver to another and will also vary depending on the acoustical impedance of the load to which the driver is coupled and may also be nonlinear. Proper operation of the system 10 requires the generation of an electrical stimulus signal that is custom designed for the specific driver 24 and the specific microphone 30 used for each system. The system 10 custom designs a stimulus signal that compensates for nonlinearities and variations in frequency response of the driver 24, microphone 30, flexible tubes 52, and associated signal conditioners such as amplifiers (not shown) and filters 22 and 36. These components are shown within the dashed line of FIG. 1 and will be referred to herein as a measurement subsystem 56. The stimulus generation procedures used by the system 10 can be applied to a stand-alone system, such as Auditory Brainstem Response (ABR) and EOAE systems. The stimulus generation procedures described herein are also needed as an initial step in the hearing assessment measurement performed by the system 10. As long as the probe assembly 50 performance is not seriously degraded such as by dropping or otherwise damaging the probe assembly, the stimulus design phase does not have to be carried out by the end-user of the system. Thus, the stimulus signal can be custom designed for the specific driver 24 and microphone 30 at the time of assembly and does not have to be repeated each time the system 10 is used. Nevertheless, the user can redesign a new stimulus, if desired.

The system 10 calculates the custom designed stimulus signal based upon measurements in a single calibration tube 60 or calibration waveguide whose cross-section area is similar to the ear-canal area in the human subject(s) to be tested, or the entryway area of any other unknown system. The length of the calibration tube is typically between 25–350 centimeters (cm), however, the length of the calibration tube is not critical so long as it permits the separation of incident and reflected signals, as will be discussed below. The calibration tube 60 has an open end 62 in which the probe assembly 50 is inserted and a closed end 64 opposite the open end 62. The acoustical characteristics of the calibration tube 60 are derived from a model of a cylindrical tube, as will be described below. The calibration tube 60 is a straight hard-walled cylindrical tube with a circular cross-section, but a flexible-walled tube or coiled cylindrical tube can also be used. Those skilled in the art can appreciate that the calibration tube 60 can be an acoustic waveguide of virtually any shape, such as square tube, oval tube, conical tube or the like, whose cross-section as a function of length is known and whose acoustical properties, including viscothermal effects, can also be derived by modeling.

The calibration tube 60 in the preferred embodiment has an open end to permit the insertion of the probe assembly 50 and a closed end that reduces the effects of ambient noise and can be modeled very accurately. However, the calibration tube 60 may be virtually any shape or dimension and have a closed end or an open end so long as the acoustical transfer characteristics of the calibration tube can be modeled. Furthermore, as will be discussed below, the incident and reflected signals may overlap acoustically if they are separable by signal processing.

Figure 3:
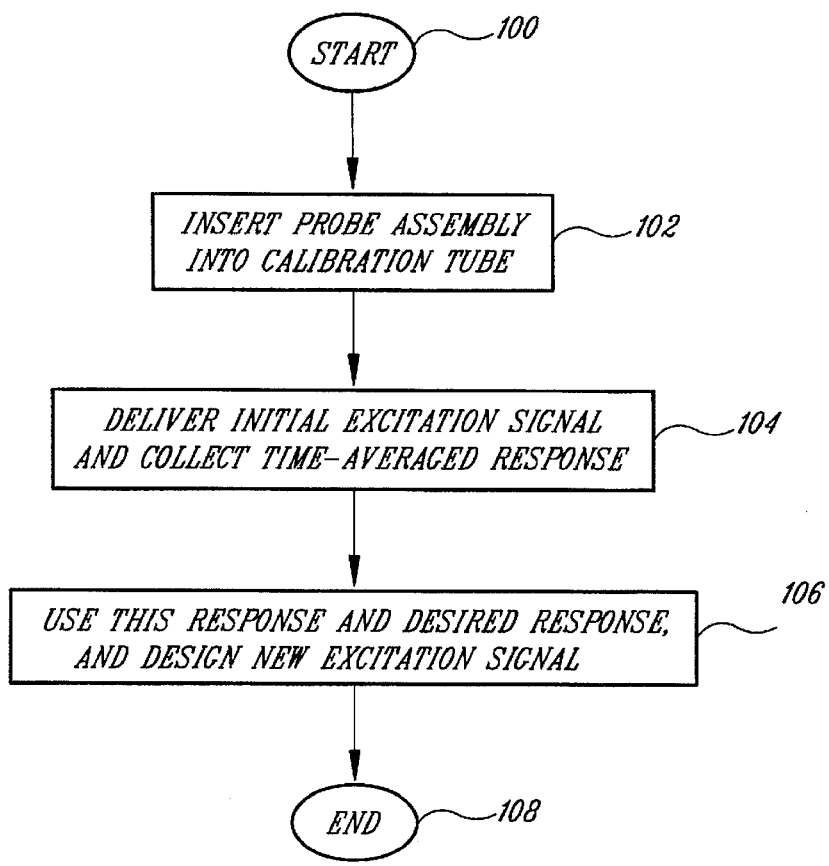
FIG. 3 is a flowchart of the stimulus design procedure used by the system of FIG. 1.

The stimulus generation procedures are described below in conjunction with the flowchart of FIG. 3. The system 10 starts at 100 with the probe assembly 50 (see FIG. 2) having unknown transfer characteristics. In step 102, the eartip 58 and the probe assembly 50 are inserted into the open end 62 of the calibration tube 60 and forms a substantially leak-proof seal of the open end. In the present embodiment, the probe assembly 50 is not vented to the ambient atmosphere. However, because the system 10 characterizes the transfer characteristics of the probe assembly 50 and other associated circuitry such as the filters 22 and 36, it automatically compensates for a well-defined pressure leak such as a vent tube. Leaks from the side of the eartip 58 are not well defined because they change from one insertion to another. These types of leaks should be avoided.

In step 104, the system 10 generates a short-duration electrical signal $e_s$ for the DAC 20 (see FIG. 1) and measure the pressure response $p_s$. The calibration tube 60 is chosen to be sufficiently long and the duration of the electrical signal $e_s$ is sufficiently short so that the initial pressure response is due only to the response of the driver 24 to the DAC signal, and is independent of sound reflections from the opposite closed end 64 of the calibration tube. The duration of the electrical signal $e_s$ is selected so that the output of the driver 24 has died away before the first reflection arrives at the probe assembly 50 from the closed end 64 of the calibration tube 60.

In step 106, the system 10 applies a signal processing algorithm, described below, that takes as input the electrical signal $e_s$, the pressure response $p_s$ and the desired incident pressure signal $p_i$ that the driver 24 should produce. For many types of hearing tests it is desired that the incident pressure signal $p_i$ generated in the ear canal in the absence of reflections from the eardrum should approximate an impulse with a finite frequency bandwidth. This describes a class of signals that in the digital domain can be designed using well-known finite impulse response (FIR) or infinite impulse response (IIR) techniques. Because these techniques are well known to those of ordinary skill in the art, they will not be described in detail herein.

Choosing a particular band-limited impulse as the desired incident pressure signal $p_i$, the system 10 uses the following signal processing algorithm to design an electrical stimulus signal $e_i$ that will cause the driver 24 to generate the desired incident pressure signal $p_i$. When the electrical stimulus signal $e_i$ is applied as input to the driver 24, the desired incident pressure signal $p_i$, or at least, a good approximation thereof, is produced as the acoustic signal 26 (see FIG. 1). This tends to reduce the influence of the frequency and phase responses of the driver 24 from subsequent processing, although the deconvolution step described below further reduces the influence of the measurement system, including the driver.

One can consider the special case where both electrical signal $e_s$ applied to the driver 24 and the desired incident pressure signal $p_i$ are equal to the impulse response d of a FIR lowpass filter, desired using the Park-McClelland method. The pressure response $p_s$ is the convolution of $e_s$ with the impulse response h of the measurement subsystem 56 and has the following form:

$$p_s = h*e_s = h*d \tag{1}$$

One can calculate the electrical signal $e_i$ producing the acoustic band-limited impulse $p_i$ via the convolution:

$$p_i = d = h*e_i. \tag{2}$$

It follows from equations (1) and (2) that $$p_s*e_i = d*d \tag{3}$$

in which $p_s$ is measured and d is known. Equation (3) is solved for $e_i$ using deconvolution (DECONV) by well-known techniques such as Singular Value Decomposition (SVD), Conjugate Gradient method (CG), Neural Network Method, Fourier transform techniques, or the like. The solution is expressed as:

$$e_i = DECONV(d*d, p_s). \tag{4}$$

It is this electrical stimulus signal $e_i$, applied to the DAC 20, that results in the band-limited impulse waveform $p_i$=d. The above example illustrates the calculation of the electrical stimulus signal $e_i$ using deconvolution in the time domain. However, the electrical stimulus signal $e_i$ may also be calculated by division in the frequency or Laplace domain. The main constraint is that the incident signal be wholly separated in time from the reflected signal. The system 10 ends the stimulus generation procedure in step 108.

Calibration Phase

Before any meaningful measurement of the acoustic response in the ear canal can be measured, the system 10 must be calibrated. To be useful, a hearing assessment device must be simple enough to be operated by a clinically trained audiologist. Existing devices, such as a tympanometer, often rely on calibration within a single cavity or resonator of known geometry. These devices are limited in the frequency range over which they can be used. In contrast, the system 10 is capable of accurate measurements over a broad range of frequencies up to 20 Kilohertz (kHz) depending on the source and microphone characteristics and the influence of the evanescent modes that describe the localized acoustic field near the probe assembly 50. Furthermore, the system 10 requires only one calibration tube 60 that is simple to use and is similar in function to the calibration cavity that is already familiar to clinicians. Prior art systems that measure the impedance, reflection coefficient, and reflection function often require two or more calibration tubes, making such systems less practical in a clinical setting.

Figure 4:
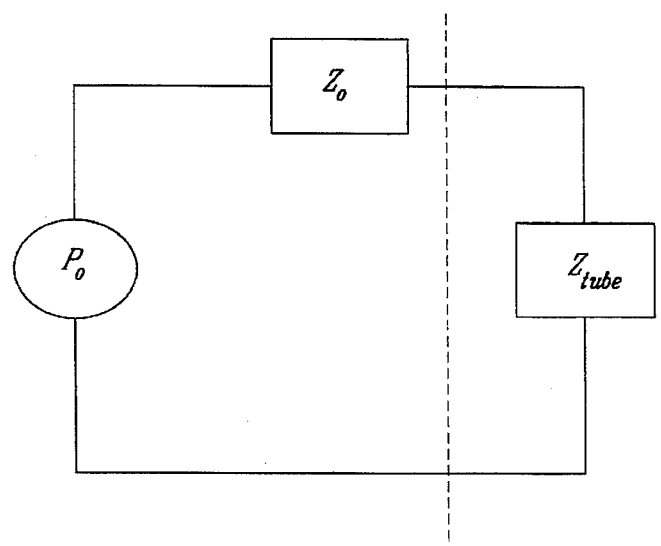
FIG. 4 is a Thevenin model of the probe assembly of the system of FIG. 1.

It is well known that the acoustic response of the measurement subsystem 56 can be represented in the frequency domain by the Thevenin equivalent pressure $p^T$ and Thevenin impedance $Z^T$. Thevenin impedance is illustrated in FIG. 4 where the measurement subsystem 56 is characterized by the Thevenin pressure $P_o$, and the Thevenin impedance $Z_o$. The calibration tube 60 is characterized by the Thevenin impedance $Z_{tube}$. The impedance $Z_{tube}$ of the calibration tube 60 can be determined analytically. Such analysis is described below. Once the Thevenin parameters of the measurement subsystem 56 is determined, it is possible to apply the measurement subsystem to an unknown acoustic termination and measure its acoustic response. In the case of the human ear, the acoustic termination comprises, the ear-canal terminated by the eardrum, middle ear, and inner ear.

These Thevenin parameters can be measured by means of a calibration procedure. For simplicity, in understanding the present invention, the Thevenin description is employed to deriving the relationships between incident and reflected pressure waves in the calibration and unknown waveguides, but the end result is independent of the Thevenin circuit parameters. This relationship is given below. A complementary representation of the Thevenin parameters is also possible in the time domain by a systematic replacement of the multiplication of transforms in the frequency domain by convolution of signals in the time domain. It is well known that this can be equally well represented by a Norton equivalent circuit.

Figure 5:
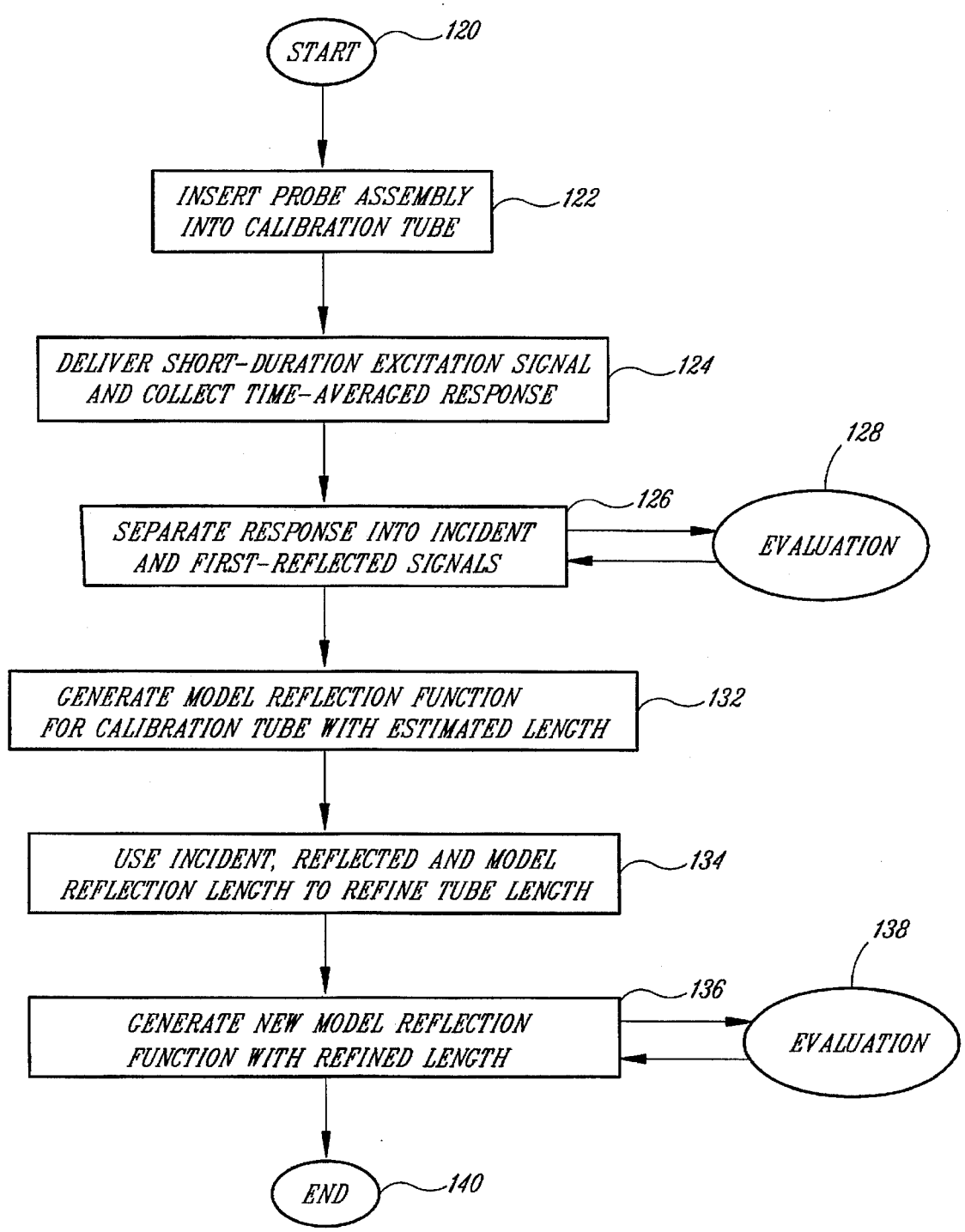
FIG. 5 is a flowchart of the calibration procedure used by the system of FIG. 1.

The calibration procedure is given below in conjunction with the flow chart of FIG. 5. The user starts in step 120 with the uncalibrated probe assembly 50 (see FIG. 2). In step 122 the user inserts the probe assembly 50 and eartip 58 into the open end 62 of the calibration tube 60 to form a substantially leak-proof seal. As discussed above, the system 10 automatically compensates for well-defined air leaks, but cannot compensate for unpredictable air leaks such as might occur along the side of the eartip 58.

In step 124, the system 10 generates the electrical stimulus signal $e_i$ (determined in the stimulus generation phase of operation) and delivers it to the DAC 20. The system 10 measures the calibration pressure response $p^c$. The length of the calibration tube 60 is sufficiently long and the duration of the electrical stimulus signal $e_i$ is sufficiently short so that the initial or incident pressure response $p_i$ is due only to the response of the driver 24 to the signal from the DAC 20, and does not include any sound reflections from the closed end 64 of the calibration tube 60. The duration of the electrical stimulus signal $e_i$ is also sufficiently short that the acoustical output of the driver 24 has died away before the first reflection from the closed end 64 of the calibration tube 60 arrives at the probe assembly 50. Thus, the system 10 measures an incident response and a separate reflected response. In step 126 the system 10 separates the pressure response into incident response and a first-reflected response. This first-reflected response is hereafter called the reflected response or reflected signal, when it is clear that higher-order reflected responses at larger delay times are not being discussed. It should be noted that, for convenience in performing the mathematical analysis, the system 10 uses the electrical stimulus signal $e_i$ derived in the stimulus generation phase as the stimulus signal in both the calibration phase and the evaluation phase. However, it is not necessary for the proper operation of the invention that the same signal be used in all three phases. It is important that the same signal be used in the calibration and evaluation phases, and the level of the electronic signal remain invariant so as to avoid nonlinear effects. These are typically associated with source transducer nonlinearity and hydrodynamical nonlinearity in the acoustic flow emerging into the calibration tube, ear canal, or other waveguide to be tested. Any signal that is sufficient short in duration relative to the length of the calibration tube 60 will be satisfactory.

The system 10 evaluates these two independent responses in step 128. It follows from the previous discussion of stimulus signal generation that $p_i^c = d$. There is no pressure response for times later than the incident response until the first reflected wave begins. After a time delay corresponding to the time for sound to propagate down the calibration tube 60 to the closed end 64, be reflected, and propagate in the calibration tube back to the probe assembly 50, this reflected pressure signal $p_r^c$ is measured. The measured pressure signal also includes contributions from the re-reflection of the wave at the probe assembly 50. Thus, the total calibration tube pressure response $p^c$ is uniquely decomposed, for times sufficiently short that the second and higher-order reflected pulses have not yet arrived, by $$p^c = p_i^c + p_r^c. \qquad (5)$$

The reflected pressure wave is influenced by the viscous and thermal attenuation in the closed end 64 of the calibration tube 60. Previous systems that use calibration tubes do not account for such effects and are thus incapable of accurate calibration and measurement. The system 10 employs an analytical representation of these viscothermal processes in terms of the reflection function $r^c$ of the closed tube. The model for this reflection function depends upon tube radius, the thermodynamic constants of air, and the tube length. A detailed analysis of the cylindrical tube model for the calibration tube 60 is provided below.

The only significant uncertainty in the measurement of the reflection function $r^c$ is in the tube length, which can vary depending on the insertion depth of the probe assembly 50. One can also regard fluctuations in the thermodynamic constants due to changes in ambient temperature as producing an equivalent change in the equivalent tube length, or else, the ambient temperature may be considered as an additional input to parameterize the temperature dependence of the thermodynamic constants in the model using well-known techniques. In step 132, the system 10 generates a model reflection function for the calibration tube 60 using an estimated value of the length L of the calibration tube. In step 134, the system 10 performs an analysis to calculate the tube length that gives the best fit between the measured reflection function and the model reflection function for the cylindrical tube. Detailed mathematical analysis of these steps are provided below. In step 136, the system 10 generates a new model reflection function for the calibration tube 60 based on an accurate determination of the length L of the calibration tube. In step 138, the system 10 uses the new model reflection function to accurately characterize the transfer characteristics of the measurement subsystem 56 (see FIG. 1). The system ends the calibration phase in step 140.

The frequency-domain representation of the Thevenin equivalent circuit is:

$$p^T - p = Z^T u, \; tm \quad (6)$$
$$p = Zu,$$

where p is the total acoustic pressure at the tip of the probe assembly 50, u is the total volume flow through the probe tip, and Z is the acoustic impedance of the air column (or ear canal) into which the probe assembly is inserted. The Thevenin impedance can be written in terms of the Thevenin reflection coefficient $R^T$, implicitly defined by:

$$Z = Z_c \frac{(1 + R^T)}{(1 - R^T)} \qquad (7)$$

where the characteristic impedance of the air column is $Z_c = \rho c/S$ such that the equilibrium air density is $\rho$, and the free-space phase velocity of sound is c, and the entryway area of the air column is S.

Because the acoustic signal applied to calibration tube 60 (or the ear canal) is a band-limited impulse it is convenient to work directly in the time domain, however, the principles of the present invention are equally applicable to calculations in the frequency domain. If one assumes that the probe assembly 50 is inserted into a cylindrical calibration tube 60 of sufficiently long length L that the source signal from the driver 24 ends before the first reflection arrives, then the initial signal detected by the microphone 30 will only be from the driver and not from reflected energy and the signal detected by the microphone after the first reflection will only be from reflections and not from the driver. The subscript 1 denotes a first time interval in which variables are non-zero only for times such that $0 \leq t < 2L/c$, and the subscript 2 denotes a second time interval in which variables are non-zero only for times $2L/c \leq t < 4L/c$. Then the Thevenin circuit equations can be transformed into the time domain with the result, $$p^{T}*\{\delta-r^{T}\}=2p_{i1}{}^{c}=2p_{1}{}^{c}, \quad (8)$$

$$p_{r2}{}^{c}=r^{c}*p_{i1}{}^{c} \quad (9)$$

where $\delta$ is the continuous-time delta-function, $r^T$ is the Thevenin reflection function, defined as the inverse Fourier transform of the Thevenin reflection coefficient $R^T$, and the reflection function $r^c$ of the cylindrical tube model is given below. Before the first reflection from the closed end 64 of the calibration tube 60 arrives, the pressure signal contains only an outgoing wave so that $p_1{}^c=p_{i_1}{}^c$. Equation (8) shows that the Thevenin source waveform $p^T$ is entirely contained in the first time interval, although the incident pressure wave depends also on the Thevenin reflection function $r^T$. The first reflected signal from the closed end 64 of the calibration tube 60 is $p_{r2}{}^c$ whose subsequent reflection from the probe assembly 50 gives rise to another outgoing wave $p_{i2}{}^c$. The Thevenin circuit relation is $$p_{i2}{}^{c}=r^{T}*p_{r2}{}^{c}=r^{T}*r^{c}*p_{1}{}^{c}, \quad (10)$$

so that the total tube pressure at the beginning of the second time interval is given by adding equations (9) and (10) with the result $$p_{2}{}^{c}=r^{c}*p_{1}{}^{c}*\{\delta+r^{T}\}. \quad (11)$$

The direct approach to solving for the Thevenin parameters is to solve equation (11) using deconvolution for $r^T$, followed by solving equation (8) using deconvolution for $p^T$. A more accurate approach is proposed below to utilize these two equations. This concludes the calibration phase of the system 10. Next is the measurement phase in which the probe assembly 50 is used to measure the acoustic response of an unknown system using the same stimulus signal as in the calibration phase. As discussed above, the stimulus signal used in the calibration and evaluation phases may conveniently be the same electrical stimulus signal $e_i$ determined in the stimulus generation phase.

The above description illustrates a technique for the characterization of the acoustic transfer characteristic of the measurement subsystem 56 (see FIG. 1) by using a stimulus signal that is short in duration so that the signal from the driver 24 has died away before the first reflected signal from the closed end of the calibration tube 60 arrives at the microphone 30. However, signal processing techniques are known in the art that permit the separation of the incident and reflected signals even though there may be some temporal overlap. A technique described in "Computer-Generated Pulse Signal Applied for Sound Measurements," by Nobuharu Aoshima, *Journal of the Acoustical Society of America* 69, 1484–88, 1981, uses a chirp as a test signal where the chirp is a time-stretched, band-limited impulse. This time-stretching factor must be explicitly known.

The presently preferred embodiment of the system uses a pulse signal so that the incident signal and the reflected signal are temporally separated. This simplifies the signal processing required by the system 10. The disadvantage of the narrow pulse signal is that, for a given signal-to-noise ratio, the pulse system requires a much higher peak amplitude than the chirp signal. This may potentially cause an overload of the driver 24. The chirp signal described in the reference cited above distributes the spectral energy over a longer time duration when compared to the band-limited impulse (i.e. pulse signals). Because the time-stretched signal has the same spectral power as the original pulse, the peak levels of the time-stretched signal are much lower than the peak levels of the corresponding short duration pulse. It is well known that peak amplitudes in the driver 24 are the primary cause of nonlinearities; the use of the time-stretched signal reduces the possibility of nonlinearities in the driver or other system components. For a given peak threshold, more power can be delivered by the driver 24 using the chirp signal than using the short duration pulse. Thus, the use of a chirp signal gives better signal-to-noise levels than the pulse-based systems. The disadvantage of the chirp signal approach is that more complex signal processing is required. However, this signal processing is well-known in the art, and need not be described in detail herein.

The chirp processing is based on the fundamental assumption that a chirp is simply a time-stretched pulse. Thus, one can begin by designing an arbitrary short duration pulse, by FIR, IIR, or other design methods, as discussed above. The chirp signal is desired by applying a conventional all-pass filter to the short duration pulse. The output in the time domain has the same spectral power as the original pulse, but the time domain waveform is stretched by the all-pass filter response. Design techniques for the all-pass filter are well-known, and will not be discussed herein.

The microphone 30 measures a response that has a similar all-pass characteristic as the chirp stimulus, but modified by the acoustic transfer characteristics of the measurement subsystem 56 and the acoustic transfer characteristics of the calibration tube 60 or other waveguide. A filter that is an inverse to the original all-pass filter is applied to the detected electrical signal 34. This inverse filter is also an all-pass filter, and its design is well-known in the art. The output from the inverse filter is a time-compressed pressure response. Thus, the chirp-like characteristic is reversed, however, the spectral level response is not modified, and the result is a short duration pressure response. So long as the impulse response of the driver 24 is much less than the time delay between the incident signal and the reflected signal in the calibration waveguide, then the incident and reflected, time-compressed, pressure responses are easily separated. These time-compressed incident and first reflected signals are processed in the same manner as the pulse signal.

Figure 8:
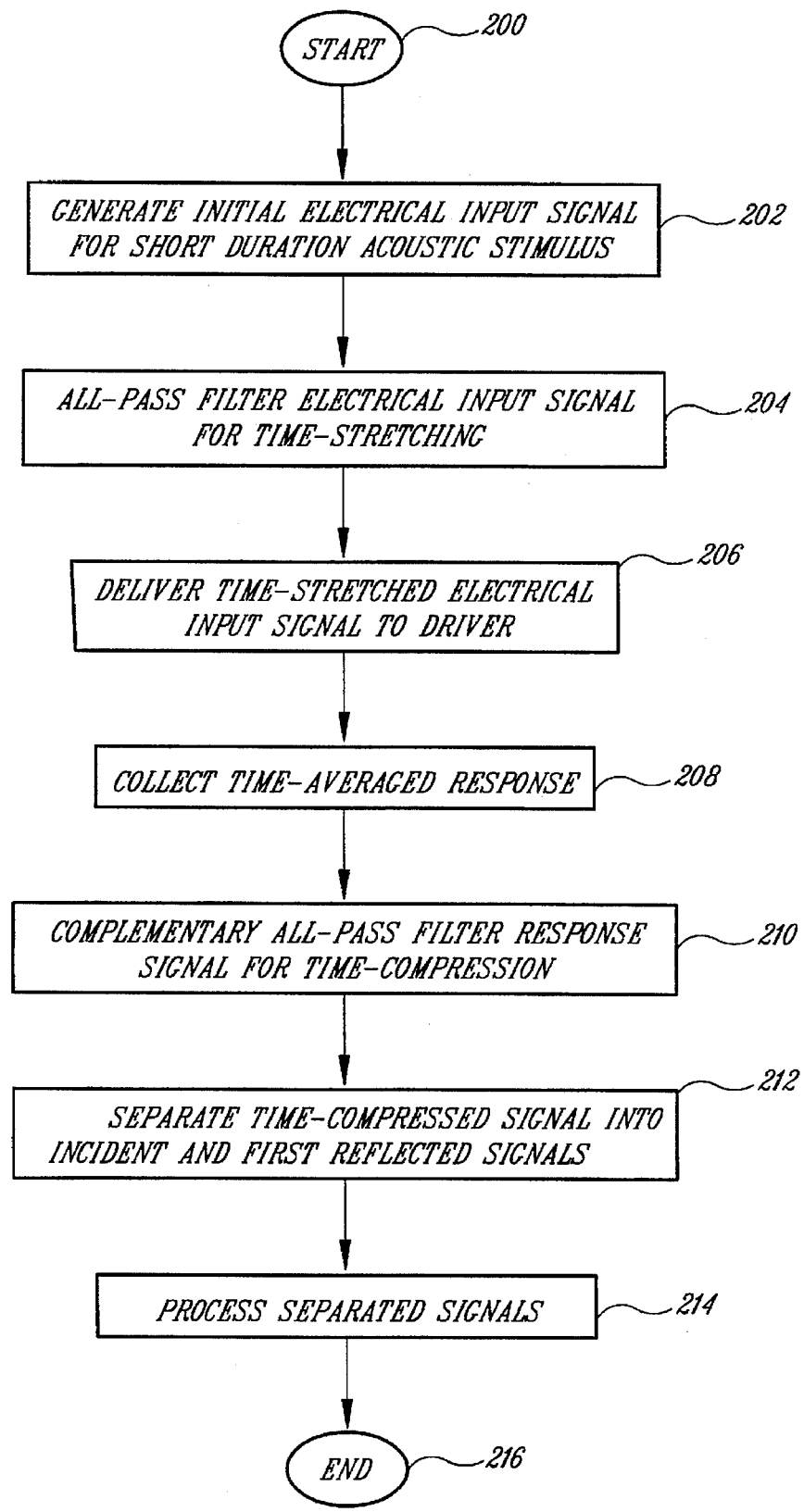
FIG. 8 is a flowchart of the time-stretching and compression measurements used by the system of FIG. 1.

The time-stretching and compression technique discussed above is described in the flow chart of FIG. 8. At the start 200, the system 10 has no time-stretched signal. In step 202, the system 10 generates an initial electrical signal input corresponding to a short duration acoustic stimulus. In step 204, the system uses an all pass filter on the electrical input signal to generate a time-stretched electrical input signal. In step 206, the system 10 delivers the time-stretched electrical input signal to the driver 24 (see FIG. 1). In step 208, the system collects a time-averaged response signal as in the manner described above. In step 210, the system filters the response signal using an inverse all-pass filter to generate a time-compressed response signal. In step 212, the system separates the time-compressed response signal into an incident signal and a first reflected signal. In step 214, the system 10 processes the separated signals in the manner previously described. The system ends the time-stretching and compression process in step 216.

The time-stretching and compression techniques discussed above may also be applied to the stimulus design phase of operation to design an electrical input signal having improved signal to noise ratio when compared to pulse techniques. The system 10 time-stretches the initial electrical signal $e_s$ using the first all-pass filter and delivers the time-stretched initial electrical signal to the driver 24. The detected electrical signal 34 is time-compressed by the inverse all-pass filter to permit the separation of the incident and first reflected signals. The separated signals are processed in the manner previously described to design the electrical stimulus signal $e_i$ that will cause the driver 24 to generate the desired incident pressure signal $p_i$. The electrical stimulus signal $e_i$ may also be time-stretched and compressed as discussed above.

Evaluation Phase

The probe assembly 50 is inserted into the ear canal and the pressure response p is measured. Because of the short length of the ear-canal and the finite sample rate of the DAC 20 and ADC 40, the incident pressure wave from the sound source and the reflected pressure wave from the eardrum are superposed in time. Prior art systems cannot readily evaluate such signals because the overlap in the stimulus signal cannot be separated for analysis. One prior art system attempts to separate the incident signal and reflected signal by placing a long tube in the patient's ear with the sound source at the end of the long tube. However, this approach is impractical in a clinical setting and is virtually impossible to use in small children. In contrast, the system 10 has determined the characteristics of the measurement subsystem 56 (see FIG. 1) in the calibration phase. This permits the system 10 to accurately analyze the overlapping incident and reflected waveforms without the use of cumbersome tubes protruding from the patient's ear. The probe assembly 50 is placed directly in the patient's ear canal in a manner identical to other audiological measurements already familiar to the clinician, such as tympanometry. The system 10 is simpler than tympanometry, because no static pressure is required.

In the frequency domain, suppose that the Thevenin parameters have been measured and the pressure response p is measured at the input to an unknown impedance Z. This impedance is calculated using the well-known "voltage divider" equation:

$$\frac{P}{P^T} = \frac{Z}{Z + Z^T} \quad (12)$$

This is transformed by changing all impedances into reflection coefficients, rearranging terms to eliminate all terms in the denominator, and inverse Fourier transforming the equation into the time domain. The resulting equation is $$2p*\{\delta - r*r^T\} = p^T*\{\delta - r^T\}*\{\delta + r\}, \quad (13)$$

where r is the reflection function of the unknown air column (e.g., the ear canal). Using the direct approach, one can substitute the functions $p^T$ and $r^T$ calculated by deconvolution and solve equation (13) for the single unknown r using deconvolution. However, the direct approach has relatively large error, because any error in the initial pair of deconvolutions contributes much larger error in the subsequent deconvolution.

A better approach, used by the system 10, is to transform equation (13) using equation (8) so that:

$$p*\{\delta - r*r^T\} = p_1^c*\{\delta + r\}, \quad (14)$$

thereby eliminating $p^T$. Equation (14) is rearranged to provide the following:

$$p - p_1^c = r*\{-p + p_1^c + p*\{\delta + r^T\}\}. \quad (15)$$

The object is to eliminate $r^T$ from this equation (15) using equation (11). This is achieved by convolving the above equation with $r^c*p^c$ with the result $$s = r*q, \quad (16)$$

where the function s is defined by $$s = r^c*p_1^c*\{p - p_1^c\}, \quad (17)$$

and where the function q is defined by $$q = -s + p*p_2^c. \quad (18)$$

Equation (16) is solved for the unknown reflection function r by a single deconvolution:

$$r = DECONV(q, s). \quad (19)$$

While the analysis described above is derived based upon the use of a Thevenin equivalent circuit, it does not depend on the explicit evaluation of these Thevenin parameters. The use of a single deconvolution is much more accurate in practical applications than using two deconvolutions of equations (8) and (11), when calculations are performed in the time domain. The corresponding frequency-domain versions of equations (16)–(18) in terms of Fourier transforms are:

$$r(f) = s(f)/q(f), \quad (20)$$

$$s(f) = r^c(f)p_1^c(f)\{p(f) - p_1^c(f)\}, \quad (21)$$

$$q(f) = -s(f) + p(f)p_2^c(f). \quad (22)$$

Cylindrical Tube Model

The reflection function r introduced earlier for a cylindrical tube of length L and cross-section radius R describes the propagation delay ($\tau = 2L/c$) and viscothermal losses for a sound wave traveling down the tube, reflecting from its closed far end, and traveling back up the tube to the probe assembly. For $t \leq \tau, r^c = 0$. For $t > \tau$, $$r^c(t) = \frac{1}{\sqrt{\pi}} \frac{A}{(t-\tau)^{3/2}} e^{-A^2/(t-\tau)}, \quad (23)$$

where $$A = \alpha \frac{L}{R}, \quad (24)$$

$$\alpha = \sqrt{\frac{l_v}{c}} + (\gamma - 1)\sqrt{\frac{l_t}{c}}, \quad (25)$$

$$l_v = \frac{\eta}{\rho c}, \quad (26)$$

$$l_t = \frac{\kappa}{\rho c C_p}, \quad (27)$$

such that $\eta$ is the shear viscosity of air, $\kappa$ is the thermal conductivity of air, $C_p$ is the specific heat of air at constant pressure, and $\gamma$ is the ratio of specific heats. The implementation uses discrete-time signal processing, so the continuous-time reflection functions must be converted to their discrete-time counterparts, by multiplication of the continuous-time function by the sample period using conventional signal processing techniques. The sample rate of the DAC 20 and the ADC 40 should be at full audio bandwidth, corresponding to sample rates in the range of 40–50 kHz.

In practical applications, these thermodynamic constants are known and the radius of the calibration tube 60 is easily measured. The tube length L is known approximately, but any insertion distance of the probe assembly 50 into the calibration tube 60 effectively reduces the acoustic length of the tube. Variations in the acoustic length of the calibration tube 60 affect the value of the propagation delay $\tau$ and the value of A thus affecting the model reflection function of equation 23. A procedure is used by the system 10 to optimally estimate the length based upon an approximate starting point. The tube model $r^c$ is calculated using equation (23) and the calibration measurements are carried out. The evaluation phase described above can be applied to the calibration tube 60 itself to estimate its reflection function. The functions s and q are calculated using the calibration tube data using equations (17–18). When the model length is correct, the signal q has a single peak. When the model length is slightly incorrect, the signal q has an additional peak at a time delay of 2L/c. Using conventional one-dimensional minimization techniques, the energy in the signal q is minimized by varying the model length L as follows:

1. Approximate the tube length L and calculate the propagation delay r to the nearest sample D. This delay is the initial value of s[D].
2. Calculate s and q. The corresponding window of the first reflection begins at s[n+D] and extends to s[n+2D−1] where s[n] denotes the value of s at the nth sample. This window brackets the second peak of q.
3. Vary the model tube length L to minimize the energy of s in the first reflection window over a range of times in such that n−D≦m≦n+2D−1. This change in L means calculating a new model reflection $r^c$ followed by recalculating s and q. Iterate until the optimum tenth L is calculated.

In this manner, the system 10 can adjust the value of the length L of the calibration tube 60 to compensate for variations in the position of the probe assembly 50 within the calibration tube. With an accurate estimate of the length L, the transfer characteristics of the measurement subsystem 56 can be accurately determined in step 138 of FIG. 5.

Figure 6:
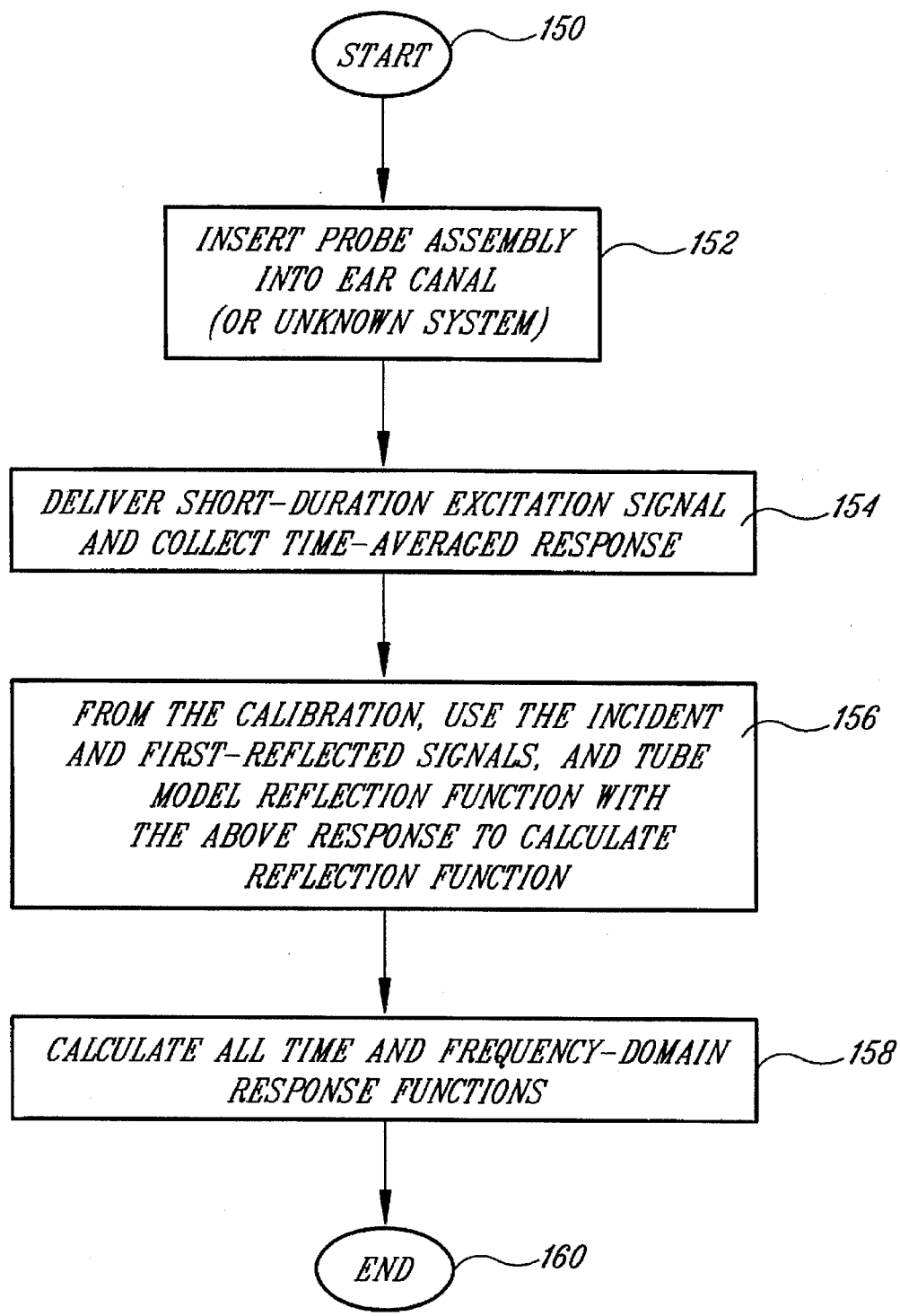
FIG. 6 is a flowchart of the linear measurement procedure used by the system of FIG. 1.

The system 10 is capable of measuring the pressure response of the ear canal or other acoustic waveguide and determining the impulse response, and other acoustic properties of the acoustic waveguide in terms of the reflection coefficient using well-known transformations. The measurement of the unknown acoustic waveguide is described below in conjunction with the flowchart of FIG. 6. At the start 150, the stimulus signal has been determined in the manner discussed above, and the system 10 has been calibrated. In step 152 the user places the probe assembly 50 (see FIG. 2) into the ear canal (or other unknown system). In step 154, the driver 24 delivers the stimulus signal, and the microphone 30 detects both the stimulus signal and reflected energy as discussed above.

In step 156 the system 10 uses the calibration data for the measurement subsystem 56 for the incident signal and the first-reflected signal, as well as the reflection function data from the calibration tube 60 to calculate the reflection function of the unknown acoustic waveguide (e.g. the ear or other system). In step 158, the system calculates the time-domain and frequency-domain response functions for the unknown system in the manner previously described. The system ends the measurement phase in step 160.

Thus, the system 10 uses the customized stimulus signal to produce a well defined acoustic stimulus and the calibration information derived from the calibration tube 60 to characterize the probe assembly 50 and its components. This information is used to determine acoustic response functions of the unknown system such as the impulse response, reflection coefficient, and other related acoustic responses in terms of the reflection function. Analyses of these acoustic response functions provides clinically important information about the state of the middle ear.

Signal processing algorithms well known in the art, such as Fourier analysis, are used to combine this acoustic response information with OAE measurements to obtain a power transfer characterization of the unknown system. Whether alone or in combination with other measurements, the acoustic response measurement provides the basis for the practical application of a computer-based hearing assessment device for humans, but also for use in animal tests. Early detection of hearing abnormalities has recently become an established health care priority. The system 10 is particularly valuable for use in testing neonates and young infants.

The system 10 may be generalized by applying an excess positive or negative static pressure to the ear canal, as is typical of tympanometry systems. Such static pressure may also be applied to the calibration-tube response measurements. Thus, the response may be obtained as a dual function of static pressure and frequency, or static pressure, and time. This representation is a generalization of traditional single-frequency or multi-frequency tympanometry.

Nonlinear component of otoreflectance

It is well known that the acoustic response of the ear to stimuli presented in the ear canal contains both a linear and a nonlinear response. The linear response is measured using the acoustic reflectance technique described above and is dominated by the mechanics of the middle ear and inner ear. It is widely thought that the nonlinear ear canal pressure response represents energy that is re-reflected from the inner ear back through the middle ear to the ear canal. This nonlinear response may involve some combination of passive and active processes in the inner ear.

Prior art systems to measure a nonlinear response focus on nonlinear changes in ear canal pressure, whether in the form of distortion product emission (DPE) or some form of otoacoustic omission. Most prior art systems are based upon a differential measurement of pressure response recorded under two or more different stimulus levels. However, this differential pressure response and the associated linear pressure response are influenced by the probe position due to the presence of standing waves in the ear canal. Moreover, the evoked OAE measurement technique resolves a nonlinear differential response only for time delays on the order of 5–20 ms after the initial quasi-impulsive stimulus, due to the ringing response of the acoustic source and the large linear response for times shorter than 5 ms. It is well known that EOAE have progressively shorter latencies (i.e., time delays) at higher frequencies. The term latency is used to refer to some measured time delay between a stimulus attribute and a response attribute. Thus, the EOAE is limited in it high frequency response by the inability to measure short-latency emissions. It is also well-known that the pressure level of EOAE and distortion product emissions varies widely between infants and adults. It is likely that variations in the linear response of the ear between infants and adults accounts for some of this discrepancy.

The nonlinear otoreflectance system 10 measures the otoreflectance in a manner that avoids these limitations. Measurement of the linear reflectance and the use of a very short duration stimulus, typical pulse durations on the order of 0.5 ms for data obtained using the stimulus design method and the Otodynamic probe assembly, allows for a nonlinear measurement for time delays on the order of 1–20 ms. This allows the measurement of sound energy emissions over a wider frequency range. Substantively simultaneous measurements of the linear and nonlinear otoreflectance allow for characterization of the linear middle ear transmission and the nonlinear inner ear response. It is well known that the energy reflectance measured in the ear canal, which is the magnitude-squared of the reflection coefficient, is substantially independent of probe position. Thus, the system 10 gives results that are substantially independent of probe-assembly position. The residual differences in travel time due to positioning the probe assembly 50 more or less distant from the eardrum are on the order of a small fraction of a millisecond. The power-based otoreflectance measurement is more fundamental than the pressure-based OAE and DPE measurements, so that more specific comparison can be made between infant and adult ear responses. In particular, acoustic power can be represented by measuring the acoustic pressure and a linear response quantity such as impedance, impulse response, reflection coefficient or reflection function. Pressure measurements alone do not characterize acoustic power transmission in the ear canal.

Two different approaches for the measurement of the nonlinear acoustic-energy response in the ear canal are described herein, both based upon a differential method using two or more stimulus levels. The first is based upon a measurement of impedance and the second is a generalization of the otoreflectance technique described above. The nonlinear component to the ear-canal impedance is measured by an extension of the frequency-domain technique known in the art.

Nonlinear impedance in the frequency domain

In addition to the measurement of the linear response of the ear, the system 10 is also capable of measuring the nonlinear response of the ear to a sound stimulus. The system 10 makes this determination by measuring the power reflected from the ear, and may potentially be used clinically and in research in place of other techniques that measure the nonlinear and linear response of the ear to sound stimuli. Prior art systems that measure nonlinear acoustic responses in the ear canal include click-evoked or tone-evoked OAE, distortion-product emissions, and nonlinear impedance due to sinusoidal-tone excitation. The latter is an alternative representation of a sinusoidal-evoked otoacoustic emission (SEOAE).

The system 10 is capable of measuring a nonlinear component to the ear-canal impedance, measured by an extension to the frequency-domain technique well known in the art. This approach requires a set of calibration tubes 60 with a range of tube diameters corresponding to the range of typical ear canal diameters. The system 10 produces a short stimulus pulse for each calibration tube 60 in the manner described above. The stimulus is presented at relatively high levels in the ear canal, for example, 80 dB SPL. The system 10 performs this calibration procedure on all calibration tubes 60 and determines the Thevenin parameters describing the measurement subsystem 56 (see FIG. 1) at this given level. The ear-canal impedance is measured in a conventional manner.

If the nonlinearities in the measurement subsystem 56 are small relative to the nonlinearities generated within the ear, then it is possible to change the level of the stimulus by a predetermined gain factor, leave the Thevenin impedance invariant, and thus change the Thevenin pressure level by the same predetermined gain factor. The ear-canal impedance is measured at this new level in the same manner previously described.

As a test of the influence of nonlinearities in the measurement system the impedance is measured in the calibration tube 60 at the same two stimulus levels to be used in the subject. If there are no nonlinearities in the measurement subsystem 56, then the resulting impedance of the unknown system (ear-canal or tube) is independent of the level of the stimulus. Subtraction of the impedance $Z_L$ measured at the lower stimulus level from the impedance $Z_H$ measured at the higher stimulus level leads to a nonlinear component of the impedance $\Delta Z$ defined by $$\Delta Z = Z_H - Z_L. \tag{25}$$

To test whether the measurement system nonlinearities are indeed negligible, the nonlinear impedance $\Delta Z$ of the cylindrical calibration tube 60 should be negligible compared to the $\Delta Z$ measured in the ear canal. If the measurement system nonlinearities are significant, then it is necessary to calibrate the system using the methods described above for each of the stimulus levels. Then, the impedance is measured at each stimulus level using its unique Thevenin parameters, and $\Delta Z$ is calculated.

Recent research indicates that the nonlinear ear canal impedance, at moderate stimulus levels, is solely a measure of the nonlinear response of the cochlea. The system 10 gives a more fundamental description of the cochlear nonlinearities than an EOAE measurement because it is based upon power measurements within the ear canal. An advantage of this technique over the conventional EOAE technique is that the linear part of the impedance describes the conductive pathway into the middle ear. The presence of a conductive impairment is detected using methods well known in the art. The nonlinear part of the impedance describes the cochlear response. This makes it possible to detect whether a clinically abnormal OAE, DP or ABR is associated with a clinically normal or abnormal middle-ear response.

It is critical that the measurement apparatus have exceptionally highly dynamic range. This is accomplished by using relatively high stimulus levels, a very sensitive microphone 30 typical of those used in EOAE measurement systems, and signal averaging of pressure responses in the ear canal. The low and high stimulus levels typically differ by 10 db. Conventional methods are used to verify that the signal-to-noise ratio in the ear canal is adequate.

The nonlinear impedance can be studied in the reflectance domain. The ear-canal impedance Z is transformed to ear-canal reflection function R via the relation:

$$R(f) = |R(f)|e^{j\phi} = (Z - Z_c)/(Z + Z_c), \tag{26}$$

where the characteristic impedance $Z_c = \rho c/S$ of the ear canal is a function of air density $\rho$, the speed of sound c and the cross-sectional area S of the ear canal are measured using conventional techniques, and where the phase of the reflection coefficient is $\phi$. This reflection function can be measured at both low and high stimulus levels, denoted by $R_L$ and $R_H$, respectively.

The nonlinear energy reflectance is defined by:

$$\epsilon = |R_H|^2 - |R_L|^2, \tag{27}$$

The reflectance group delay $\tau_g$ is defined in terms of the phase by $$\tau_g = -\frac{d\phi}{d\omega}, \tag{28}$$

where $\omega$ is the radian frequency. As is well known to those of ordinary skill in the art, the group delay (at frequency $f$) is the time delay between an initial short-duration waveform envelope, with spectrum centered about a particular frequency $f$, and the corresponding maximum in the reflected waveform envelope. The nonlinear reflectance group delay is defined by $$\Delta \tau_g = \tau_{gH} - \tau_{gL}, \tag{29}$$

where $\tau_{gH}$ and $\tau_{gL}$ are the group delays measured for the high level and low level stimuli, respectively.

The energy reflectance is the ratio of reflected energy to incident energy in the ear canal. Its nonlinear component, $\epsilon$, is the fraction of energy reflected due to the nonlinear cochlear component. An increase in energy reflectance of the high level stimulus is evidence for active sources of energy within the cochlea, unless it is accompanied by a decrease in reflectance at some other frequency. Such a decrease might suggest nonlinear conversion of energy from one frequency band to another. The energy reflectance of a linear or nonlinear passive system, in the absence of mean flow effects, is always less than unity. The total reflected energy per unit incident energy density is the integral of energy reflectance over frequency. An increase in this integrated energy with signal level is indirect evidence for an active process. The group delay provides a direct measure of the latency of the reflected energy.

Direct measurement of nonlinear reflectance

The second approach to measure the nonlinear response is based on reflectance in the time-domain. The stimulus is presented at different input levels, and responses are measured at these different levels. The probe assembly 50 is calibrated at each of these input levels using the procedures described in the linear reflection function measurement method discussed above. The dominant nonlinearity in the probe assembly 50 is the nonlinear response of the driver 24. Nonlinear effects in the microphone 30 are typically negligible. The reflection function can be measured for stimuli ranging from high level down to very low levels using the calibration data measured for the selected level.

The calibration with a single calibration tube 60 is simpler than in the nonlinear impedance measurement technique discussed above. Standing waves in the nonlinear impedance measurement effectively limit measurements to relatively high stimulus levels. However, the reflectance measurement of the system 10 is not as susceptible to standing waves and thus it may be possible to measure ear canal responses at much lower stimuli levels where the nonlinear effects become nearly as large as the linear effects.

Because this technique is simpler (using only a single calibration tube) than the multi-tube impedance measurement describe above and capable of measuring responses over a wider range of stimuli levels, it is anticipated that its performance will be superior to the first method.

In one embodiment, the signal is designed to be a band-limited impulse at each of two or more signal levels. The stimulus design phase described above is used independently at two or more signal levels. The simplest embodiment uses two signal levels, high and low. In the preferred embodiment, the analog signal 18 (see FIG. 1), from the DAC 20 interleaves the low level and high level signals in a continuous stream. A template is formed of a single occurrence of the high level signal with M occurrences of the low level signal. Typical values of M are in the range of 2-4, for amplitude ratio values G in the range 2-4. The reason that M is chosen greater than 1 is because the response measured under the low level condition has a reduced signal to noise level, and thus requires additional signal averaging to achieve a comparable reduction in noise. A template of interleaved low level and high level responses are obtained from the detected electrical signal 30 and digitally encoded using the ADC and the signal processor. The mean and variance of the low level and the high level signals are separately calculated, by time-averaging over sets of templates. The mean response at low level is used to design a low level band-limited impulse, and the mean response at high level is used to design a high level band limited impulse, that is scaled in amplitude by the ratio G. The resulting low and high level electrical input signals that approximate the band-limited impulses are interleaved in a continuous template as above.

Figure 7:
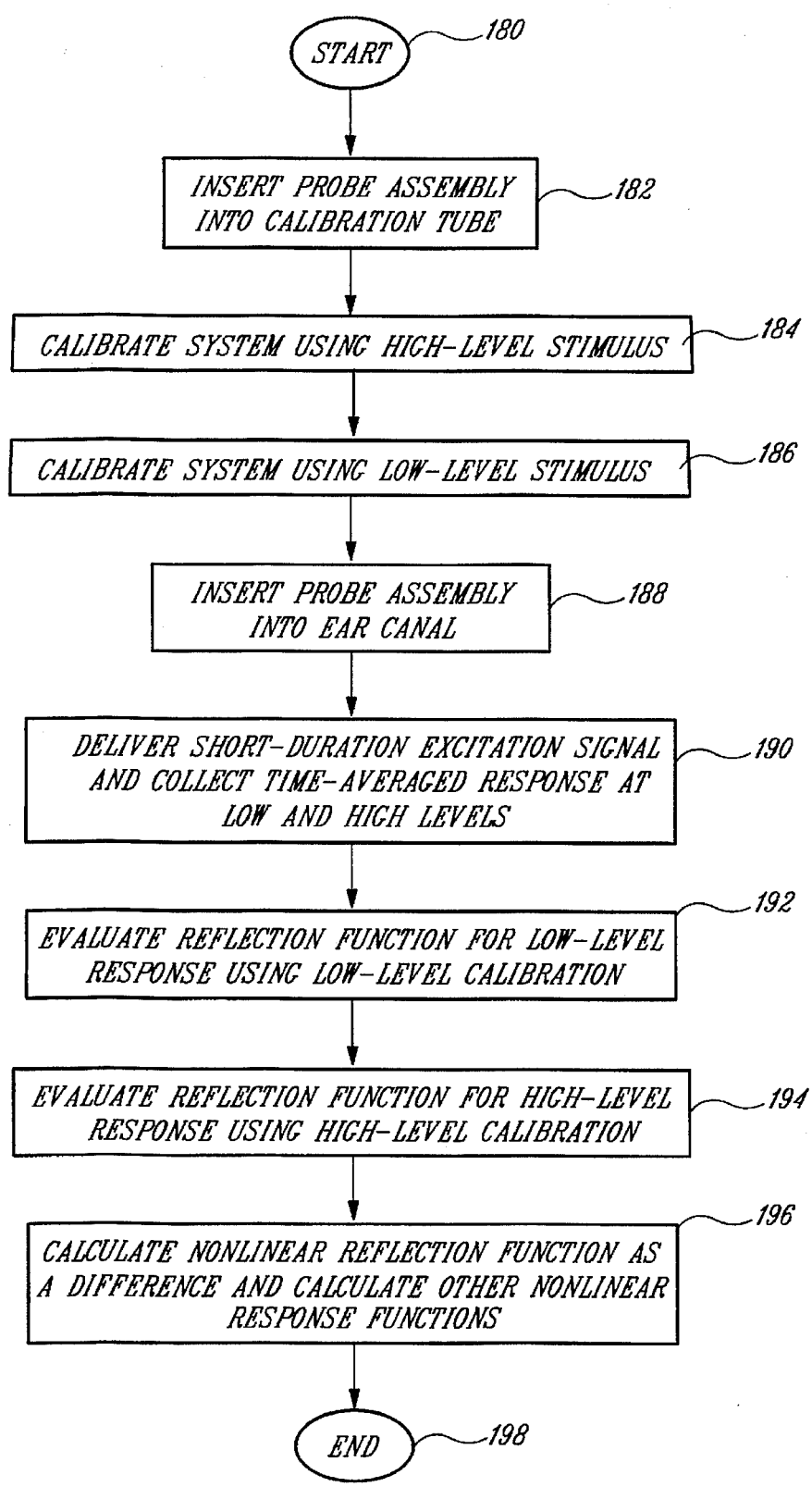
FIG. 7 is a flowchart of the nonlinear measurement procedure used by the system of FIG. 1.

The measurement of the nonlinear otoreflectance is shown in the flow chart of FIG. 7. At the start 180, the probe assembly 50 is uncalibrated. In step 182, the probe assembly 50 is inserted in the calibration tube 60. The calibration phase of the nonlinear otoreflectance system consists of measuring the incident and reflected signals in the calibration tube 60 under both low level and high level conditions in the manner described above. The pressure responses to the template of electrical signals themselves form a template of responses. In step 184, the system 10 calibrates the probe assembly 50 using a high level stimulus. In step 186, the system 10 calibrates the measurement subsystem 56 (see FIG. 1) using a high level stimulus. In step 186, the system 10 calibrates the measurement subsystem 56 using a low level stimulus.

In step 188, the probe assembly 50 is inserted into the ear canal. The evaluation phase of the nonlinear otoreflectance system consists of measuring the pressure response when the probe assembly 50 is inserted into the ear canal, and the responses form a template of responses to the low level and the high level stimuli. In step 190, the system 10 delivers short duration excitation signals and collects time averaged responses to the low level and high level stimuli. In step 192, the system 10 evaluates the reflection function for the low level response, using the low level calibration determined in step 186. In step 194, the system evaluates the reflection function for the high level response using the high level calibration determined in step 184. As in the evaluation phase of the linear reflectance method described above, the unknown reflection function in the ear is calculated from equation 19 using a signal deconvolution at each of the two stimulus levels. In step 196, the system 10 calculates the nonlinear reflection function as a difference of the linear reflection functions at the two stimulus levels. The system may also calculate other nonlinear response functions. The system 10 ends the nonlinear measurement in step 198.

The reflection function measured with the low level (high level) electrical stimulus is denoted by $r_L$ ($r_H$). In the absence of nonlinear effects, the difference $\Delta r = r_H - r_L$ should be zero between the mean high-level response and the boosted low level response. Thus, the calculated difference is a differential measure of the nonlinear contribution to the reflectance. The linear contribution to the reflectance may either be taken to be $(r_H + r_L)/2$ or $r_H$. The former choice is the mean response, while the latter choice is advantageous because the cochlear nonlinearity saturates at moderately high signal levels. In waveguides such as musical instrument air columns that behave linearly at low excitation levels, the linear reflectance is approximated by $r_L$. This embodiment of the otoreflectance system 10 gives a substantially simultaneous measurement of the linear and the nonlinear responses.

For improved noise rejection, two sub-ensembles of responses at each stimulus level can be maintained to test for noise fluctuations and used with a threshold or cross-correlation criterion to eliminate noisy sections of data.

Prior art systems utilize a nonlinear, differential measurement of pressure. As is well known, pressure measurements are susceptible to variations due to standing waves within the ear canal. This variation is highly dependent on the position of the probe within the ear canal and can cause large errors in a differential nonlinear measurement. In contrast, the system 10 uses no direct subtraction of pressure response. Instead, the reflectances are calculated at each of the two (or more) stimulus levels, and it is the reflectance responses that are subtracted to form a nonlinear, differential response. This constitutes a differential power-based measure. Power measurements used by the system 10 are far less susceptible to variations due to the positioning of the probe assembly 50 within the ear canal. Any deconvolution method described earlier for the acoustic reflectance system can also be used for this otoreflectance system. Prior art systems are incapable of measurements with short latencies due to their inability to separate the response of the measurement system from the response of the unknown system. The deconvolution process of the system 10 removes the effect of the measurement subsystem 56 (see FIG. 1) from the measurement of the unknown system. This permits the measurement of short latency responses from the unknown system. In the auditory system, measurement of the nonlinear response is possible at much higher frequencies (up to 20 kHz) than is possible in the prior art. The response can be transformed between frequency and time domains, and the reflectance can be transformed into impedance or impulse response (the Fourier transform of the impedance) by well-known transformations. The nonlinear response measurements are shown in the above examples as the difference between linear responses at two different stimulus levels. Those skilled in the art can appreciate that difference measurements can be made at more than two stimulus levels to produce a more complete characterization of the nonlinear response.

In alternative embodiments, the low level and high-level conditions can be separately measured, that is, non-interleaved, or can be combined in any convenient manner, for example, a random interleave can be used.

The linear response of the auditory, system to either a pulse signal or chirp stimulus signal should be identical in the absence of noise. However, it is known in the art that the nonlinear response of the auditory system will generally vary, with the choice of stimulus. For example, impulse excitation of the nonlinear system may provide different information than a sinusoidal excitation of the same system. The nonlinear measurement system discussed herein is based on a differential procedure at a number of different stimulus excitation levels. The impedance or reflectance is measured as a function of level, using the same stimulus signal waveform and changing only the stimulus signal level. As one skilled in the art can appreciate, the nonlinear response of the cochlea to a pulse-like signal and a chirp-like signal may differ so that the two types of excitation signals may provide complementary information on the cochlea. The present invention is not to be limited by the specific form of the stimulus signal.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for the generation of an acoustic stimulus signal having a predetermined pressure response, the system comprising:

an acoustic calibration waveguide having known acoustic transfer characteristics;

a probe assembly positionable in said acoustic calibration waveguide;

an acoustic source within said probe assembly to produce an acoustic stimulus in said acoustic calibration waveguide in response to an electrical input signal:

an acoustic energy detector within said probe assembly to detect acoustic energy signals and convert said detected acoustic energy signals to detected electrical signals:

a stimulus generator coupled to said acoustic source to generate said electrical input signal, said stimulus generator generating an electrical test signal having a selected duration so that an incident signal from said acoustic source is separable from a reflected signal reflected from said acoustic calibration waveguide a signal processor to receive said detected electrical signals and calculate an incident signal response and a reflected signal response for said acoustic calibration waveguide, said incident and reflected signal responses forming a total response, said signal processor further receiving said electrical test signal, and a desired total response to determine an electrical stimulus signal that will produce said desired total response when said electrical stimulus signal is applied to said acoustic source, whereby said electrical stimulus signal compensates for effects of said acoustic source and said acoustic energy detector.

2. The system of claim 1 wherein said electrical input signal has a selected duration so that said acoustic stimulus is a short duration sound field having a duration less than a propagation time required for said acoustic stimulus to travel from said acoustic source and be reflected from said acoustic calibration waveguide back to said acoustic energy detector whereby said incident and reflected signals are substantially non-overlapping in time.

3. The system of claim 1 wherein said stimulus generator generates a short duration pulse that is time-stretched to form said electrical input signal, said signal processor time-compressing detected electrical signal to calculate said incident signal response and said reflected signal response.

4. The system of claim 3 wherein said short duration pulse is time-stretched by a first all-pass filter and said detected electrical signal is time-compressed by a second all-pass filter that is inverse to said first all-pass filter.

5. The system of claim 1 wherein said acoustic calibration waveguide has predetermined dimensions including a tenth and a cross-sectional area as a function of said length.

6. The system of claim 5 wherein said length is at least 25 centimeters.

7. The system of claim 5 wherein said acoustic calibration waveguide is a cylindrical tube with said cross-sectional area having a constant value as a function of said length.

8. The system of claim 1 wherein said acoustic calibration waveguide is a hardwalled acoustic calibration waveguide.

9. The system of claim 1 wherein said probe assembly substantially seals said acoustic calibration waveguide from ambient atmosphere.

10. The system of claim 1, further including storage means for storing said electrical stimulus signal.

11. The system of claim 1 wherein said stimulus generator applies said electrical stimulus signal to said acoustic source when said probe assembly is positioned in proximity with an acoustic waveguide with unknown acoustic properties, said detected electrical signals being indicative of said unknown acoustic properties, said signal processor using said detected electrical signals to determine said unknown acoustic properties.

12. The system of claim 11 wherein said determination of said unknown acoustic properties includes a determination of a reflection function of said unknown acoustic waveguide.

13. The system of claim 11 wherein said unknown acoustic waveguide is a human ear comprising an ear canal, a middle ear, and an inner ear.

14. The system of claim 1 wherein said acoustic calibration waveguide has predetermined dimensions including a length and a cross-sectional area as a function of said length, said signal processor determining a functional length of said acoustic calibration waveguide by reiteratively calculating a value for a reflection coefficient as a function of said functional length to minimize the difference between said reflection coefficient value and a reflection coefficient model value for said acoustic calibration waveguide.

15. The system of claim 14 wherein said acoustic calibration waveguide is a cylindrical tube with said cross-sectional area having a constant value as a function of said tube length.

16. The system of claim 1 wherein said acoustic calibration waveguide is a hardwalled acoustic calibration waveguide.

17. The system of claim 1 wherein said signal processor determines said electrical stimulus signal using deconvolution.

18. The system of claim 17 wherein said deconvolution is a neural network deconvolution.

19. The system of claim 17 wherein said deconvolution is selected from a group comprising singular value decomposition, conjugate gradient or Fourier analysis.

20. The system of claim 1 wherein said desired total response signal is a band-limited impulse signal, said signal processor determining said electrical stimulus signal using an infinite impulse response signal.

21. The system of claim 1 wherein said desired total response signal is a band-limited impulse signal, said signal processor determining said electrical stimulus signal using a finite impulse response signal.

22. The system of claim 1 wherein said electrical test signal and said desired total response signal are both equal to an impulse response of a finite impulse response (FIR) lowpass filter wherein said impulse response equals the convolution of said electrical test signal and an impulse response of said acoustic source, said signal processor calculating said electrical stimulus signal by deconvolution of said impulse response and said total pressure response.

23. The system of claim 22 wherein said deconvolution is calculated in the time domain.

24. The system of claim 22 wherein said deconvolution uses a process selected from a group comprising a singular value deconvolution, neural network deconvolution, conjugate gradient, and Fourier analysis to determine said electrical input signal.

25. A method for the generation of an acoustic stimulus signal having a predetermined pressure response, the method comprising the steps of:

positioning a probe assembly in proximity, with an acoustic calibration waveguide having known acoustic transfer characteristics, said acoustic calibration waveguide having predetermined dimensions and having first and second ends, said first end being open and said second end being closed, said probe assembly being positioned in proximity with said open end;

producing an acoustic stimulus in response to an electrical input signal to an acoustic source within said probe assembly, and delivering said acoustic stimulus to said acoustic calibration waveguide;

detecting acoustic energy signals using an acoustic energy detector within said probe assembly, and convening said detected acoustic energy signals to detected electrical signals;

generating said electrical input signal with a selected duration so that said acoustic energy detector has an initial response due only to acoustic energy from said acoustic source and not from acoustic energy reflected from said closed end of said acoustic calibration waveguide, said acoustic energy detector further having a subsequent response due only to acoustic energy reflected from said closed end of said acoustic calibration waveguide and not from acoustic energy from said acoustic source, said initial response and said subsequent response forming a total response; and processing said detected electrical signals corresponding to said total response, said electrical test signal, and a desired total response to determine an electrical stimulus signal that will produce said desired total response when said electrical stimulus signal is applied to said acoustic source, whereby said electrical stimulus signal compensates for effects of said acoustic source and said acoustic energy detector.

26. The method of claim 25, further including the step of determining acoustic properties of an unknown acoustic waveguide by applying said electrical stimulus signal to said acoustic source when said probe assembly is positioned in proximity with said unknown acoustic waveguide, said detected electrical signals being indicative of said acoustical properties of said unknown acoustic waveguide.

27. The method of claim 26 wherein said acoustic properties of said unknown acoustic waveguide includes a determination of a reflection function of said unknown acoustic waveguide.

28. The method of claim 26 wherein said unknown acoustic waveguide is a human ear comprising an ear canal, a middle ear, and an inner ear, said acoustical properties including a linear response of said middle ear.

29. The method of claim 25 wherein said acoustic calibration waveguide is a cylindrical calibration tube.

30. The method of claim 25 wherein said predetermined dimensions include a length and a cross-sectional area as a function of said length, the method further including the step of determining a functional length of said acoustic calibration waveguide by reiteratively calculating a value for a reflection coefficient as a function of said functional length to minimize the difference between said reflection coefficient value and a reflection coefficient model value for said acoustic calibration waveguide.

* * * * *

UNITED STATES PATENT AND TRADEMARK OFFICE
CERTIFICATE OF CORRECTION

PATENT NO.     : 5,651,371
DATED          : July 29, 1997
INVENTOR(S)    : Douglas H. Keefe It is certified that error appears in the above identified patent and that said Letters Patent is hereby corrected as shown below:

In column 24, claim 25, line 6, after "and" delete "convening" and substitute therefore -- converting --.

Signed and Sealed this

Fourth Day of August, 1998

*Attest:*

*Attesting Officer*

BRUCE LEHMAN
*Commissioner of Patents and Trademarks*